(12) United States Patent
Wiser et al.

(10) Patent No.: US 11,033,461 B2
(45) Date of Patent: Jun. 15, 2021

(54) SYSTEMS AND METHODS FOR MONITORING MEDICATION ADHERENCE AND COMPLIANCE

(71) Applicant: Verily Life Sciences LLC, South San Francisco, CA (US)

(72) Inventors: Robert Wiser, San Francisco, CA (US); Daniel Barrows, Sunnyvale, CA (US); Jeremy Emken, San Jose, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 16/582,613

(22) Filed: Sep. 25, 2019

(65) Prior Publication Data

US 2020/0016033 A1 Jan. 16, 2020

Related U.S. Application Data

(63) Continuation of application No. 15/331,097, filed on Oct. 21, 2016, now Pat. No. 10,456,326.

(51) Int. Cl.
*A61J 7/04* (2006.01)
*A61J 1/03* (2006.01)
(Continued)

(52) U.S. Cl.
CPC .............. *A61J 7/0436* (2015.05); *A61J 7/04* (2013.01); *A61J 1/00* (2013.01); *A61J 1/03* (2013.01); *G16H 20/10* (2018.01); *G16H 40/67* (2018.01)

(58) Field of Classification Search
CPC ........ A61J 1/00; A61J 1/03; A61J 7/00; A61J 1/04; A61J 7/0409; A61J 7/0418;
(Continued)

(56) References Cited

U.S. PATENT DOCUMENTS 5,313,439 A 5/1994 Albeck
6,317,390 B1 11/2001 Cardoza
(Continued)

FOREIGN PATENT DOCUMENTS

WO 2011074744 6/2011
WO 2018075211 4/2018

OTHER PUBLICATIONS

U.S. Appl. No. 15/331,097 , "Non-Final Office Action", dated Jan. 18, 2019, 12 pages.
(Continued)

*Primary Examiner* — Van T Trieu
(74) *Attorney, Agent, or Firm* — Kilpatrick Townsend & Stockton LLP

(57) ABSTRACT

Systems and methods for monitoring medication adherence and compliance are provided. A medication monitoring system may include a medication container, a cover, and a beacon system. The beacon system may include a beacon that transmits a wireless signal when the cover is removed from the medication container. A method for monitoring medication adherence and compliance may include detecting when a cover of a medication container is removed from the medication container. The method may further include transmitting based on the detection, a signal from a beacon to a remote device, which indicates the opening of the medication container.

28 Claims, 5 Drawing Sheets

(51) Int. Cl.
*A61J 1/00* (2006.01)
*G16H 20/10* (2018.01)
*G16H 40/67* (2018.01)

(58) Field of Classification Search
CPC ...... A61J 7/0427; A61J 7/0436; A61J 7/0481; A61J 7/0545; G06F 19/34; G06F 19/3456; G06F 19/3462
See application file for complete search history.

(56) References Cited

U.S. PATENT DOCUMENTS

| | | | |
|---|---|---|---|
| 2009/0048871 A1* | 2/2009 | Skomra | G06F 19/3456 705/3 |
| 2009/0261011 A1 | 10/2009 | Imai et al. | |
| 2011/0060448 A1* | 3/2011 | Gotou | G16H 20/13 700/215 |
| 2014/0243749 A1 | 8/2014 | Edwards et al. | |
| 2016/0074284 A1 | 3/2016 | Despa et al. | |
| 2016/0106622 A1* | 4/2016 | Van De Wouw | G06F 19/3456 206/534 |
| 2016/0239635 A1* | 8/2016 | Fateh | G06F 19/3462 |
| 2016/0327427 A1* | 11/2016 | Briones | B65D 51/248 |
| 2017/0056289 A1 | 3/2017 | Tsuno | |
| 2017/0095405 A1* | 4/2017 | Afsarifard | G06F 19/3462 |
| 2017/0300659 A1* | 10/2017 | Ziv | G06F 19/326 |
| 2018/0113993 A1 | 4/2018 | Wiser et al. | |

OTHER PUBLICATIONS

U.S. Appl. No. 15/331,097, "Notice of Allowance", dated Jun. 17, 2019, 7 pages.
PCT/US2017/054099, "International Preliminary Report on Patentability", dated May 2, 2019, 10 pages.
PCT/US2017/054099, "International Search Report and Written Opinion", dated Mar. 16, 2018, 16 pages.
PCT/US2017/054099, "Invitation to Pay Add'l Fees and Partial Search Report", dated Dec. 15, 2017, 7 pages.
Chinese Application No. 201790001346.0, Notice of Decision to Grant, dated Apr. 8, 2020, 2 pages.

* cited by examiner

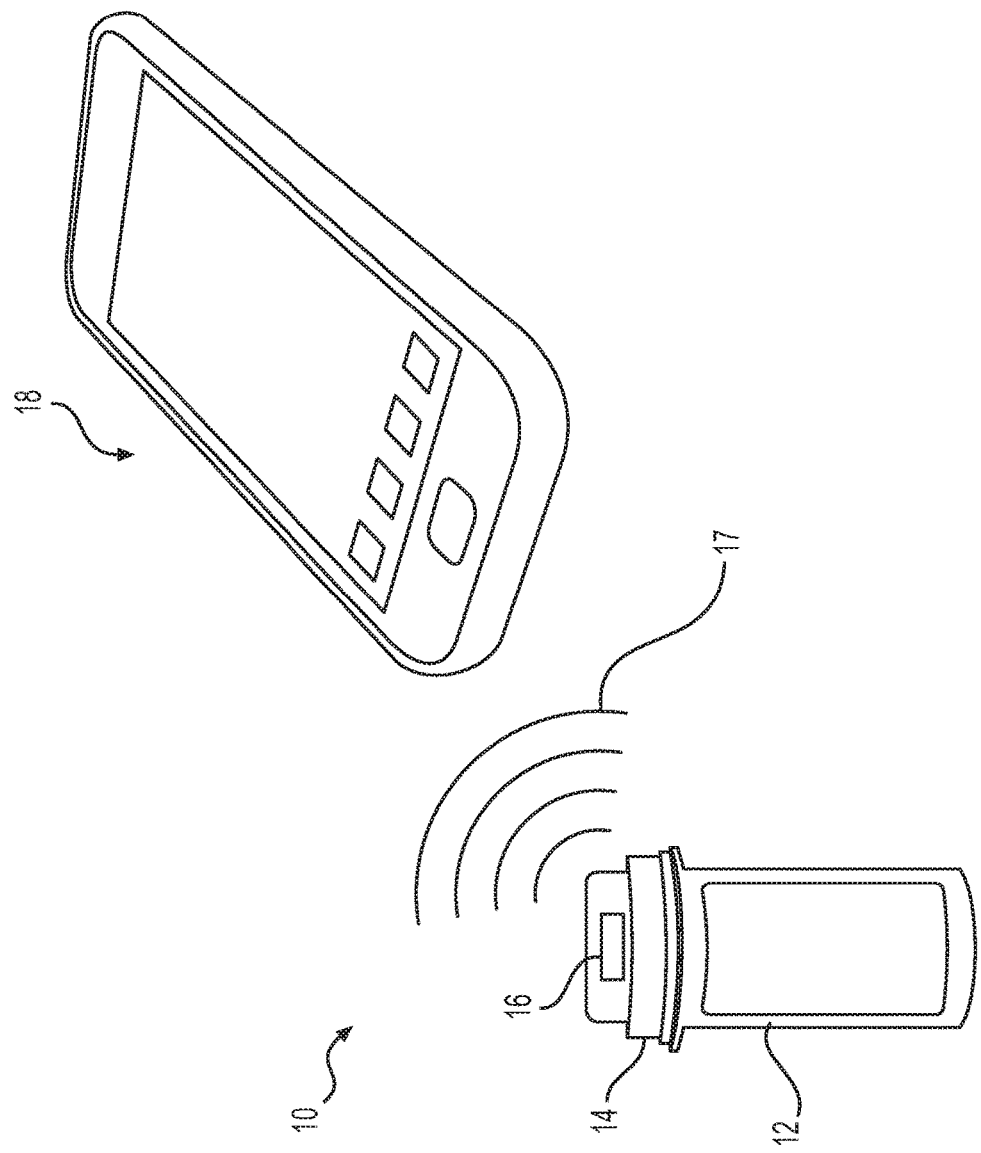

SYSTEMS AND METHODS FOR MONITORING MEDICATION ADHERENCE AND COMPLIANCE

CROSS-REFERENCE TO RELATED APPLICATIONS

This application is a continuation of U.S. patent application Ser. No. 15/331,097, filed Oct. 21, 2016, titled "Systems and Methods for Monitoring Medication Adherence and Compliance," now U.S. Pat. No. 10,456,326, the entirety of which is hereby incorporated by reference.

FIELD

The present disclosure relates generally to the field of medication adherence and compliance, and more particularly, to systems and methods for monitoring medication adherence and compliance.

BACKGROUND

Medication adherence is the act of timely filling or refilling prescriptions for medications. Medication compliance is the act of taking medication on schedule or as prescribed by a physician. According to the National Council on Patient Information and Education, poor medication adherence can lead to unnecessary disease progression and complications, reduced functional abilities and quality of life, additional medical costs and physician visits, increased use of expensive, specialized medical resources, and unneeded medication changes. Medication noncompliance can also lead to these and other adverse effects—the average length of hospital stays due to medication noncompliance is 4.2 days. In the United States, 12 percent of people are 0% compliant (i.e., do not take their medication at all) even after they fill the prescription (i.e., are adherent).

There are a number of reasons why people are nonadherent and/or noncompliant with their medication regimen. The various factors that interfere with medication adherence and compliance include: social/economic-related factors such as age, race, economic status, literacy and costs; individual factors such as forgetfulness, treatment anxiety, misunderstood instructions and fear of addiction; medication-related factors such as the length or complexity of the treatment and the side-effects of the medication; and condition-related factors such as comorbidities and disabilities, and the overall severity of the condition.

By some estimates, up to 50% of patients are noncompliant to some extent, making it difficult for doctors to assess if a medication regimen is effective. If the patient is not accurately or truthfully reporting his or her compliance, doctors do not have a means of obtaining more accurate information. Furthermore, patient tracking of which medications to take and when can be cumbersome and can be confusing for some patients.

There are various techniques and systems that try and improve patient adherence and/or compliance. For instance, some devices have been developed for mounting on pill bottles, including for example, devices that detect opening and closing of the device and alert a patient when to take a medication using a timer. Although, these prior art approaches provide at least some means to improve medication adherence and compliance, there is much room for significant advancement and improvement in the technology in order to reduce the cost and friction to the patient while improving the functionality/

SUMMARY

Embodiments of the present disclosure include systems and methods for monitoring medical adherence and compliance. Embodiments of this disclosure include, for example, medication containers (e.g., pill packages, bottles, etc.) with beacon transponders incorporated into the packaging (e.g., a cap or cover).

In one aspect, the present disclosure is directed to a medication monitoring system that includes a medication container and a cover. The medication monitoring system may also include a beacon system. The beacon system may include a beacon that transmits a wireless signal when the cover is removed from the medication container.

In another aspect, the present disclosure is directed to a method for monitoring medication adherence and compliance. The method may include detecting when a cover of a medication container is removed from the medication container. The method may also include transmitting based on the detection, a wireless signal from a beacon to a remote device, which indicates the opening of the medication container.

In another aspect, the present disclosure is directed to a medication monitoring system that includes a medication container and a cover. The medication monitoring system may also include a beacon system, which may include a beacon that transmits a wireless signal when the cover is removed from the medication container. The beacon system may also include two electrical contacts, and a rim of the medication container may include a conductor that connects the two electrical contacts when the cover is installed on the medication container.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 1 is a schematic illustration of a medication adherence and compliance system having a beacon system, according to an exemplary embodiment.

DETAILED DESCRIPTION

Figure 2A:
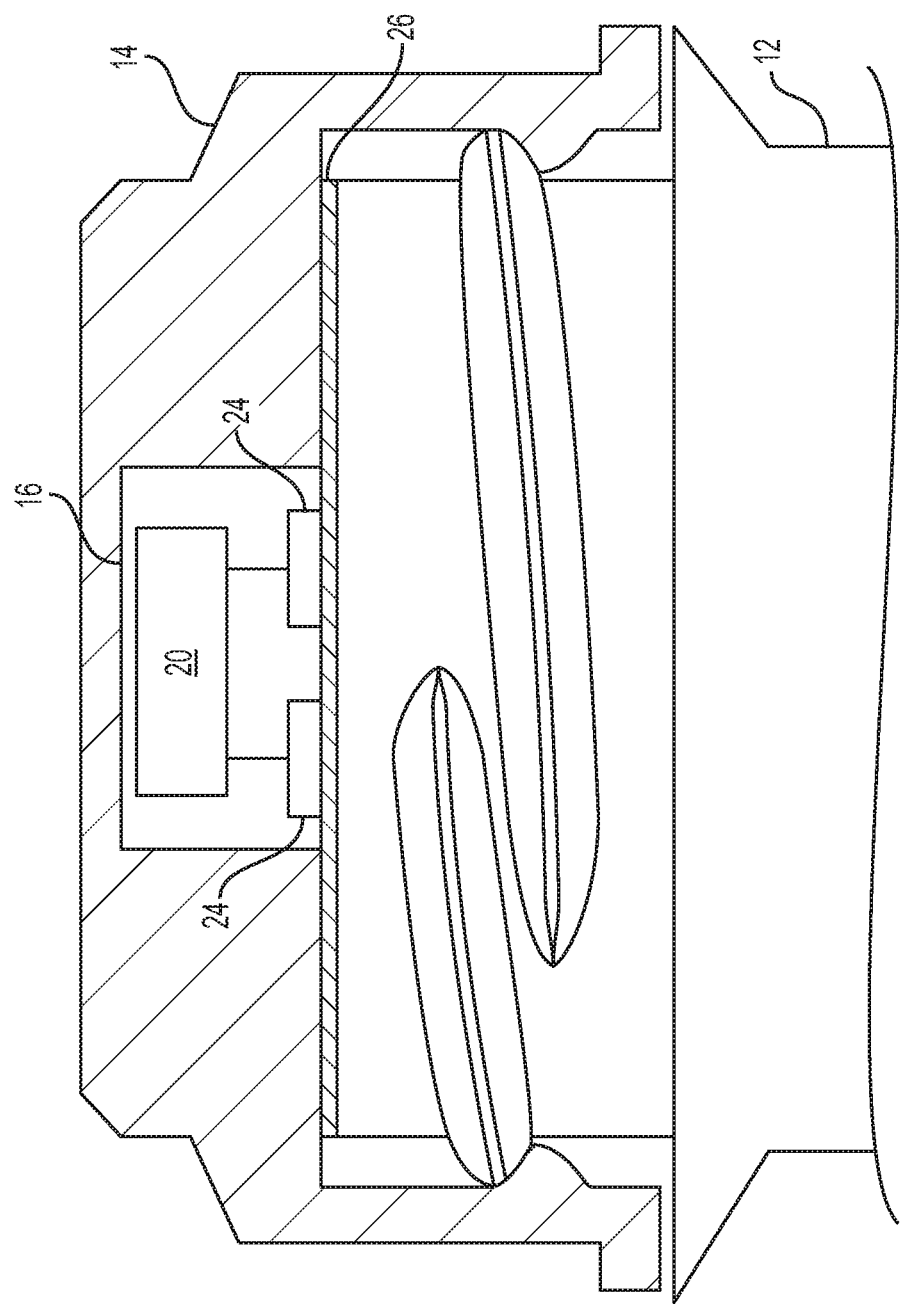
FIG. 2A is a schematic illustration of the beacon system of FIG. 1, according to an exemplary embodiment.

The disclosed embodiments relate to medication containers (e.g., bottles) including beacons signaling when a medication container has been opened by a user. As a result, the beacon's signals can be monitored to indicate patient adherence and compliance with a medical regimen.

Reference will now be made in detail to embodiments of the present disclosure, examples of which are illustrated in the accompanying drawings. Where possible, the same reference numbers will be used throughout the drawings to refer to the same or like parts.

FIG. 1 depicts an exemplary embodiment of a medication adherence and compliance system 10, which in an illustrative embodiment may be a medication container, for example, a bottle 12 and a cover, for example, a cap 14, and a beacon system 16. Bottle 12 may be used to contain a medication (e.g., pills, tablets, capsules, suppositories, ampoules, subpackets of powder, etc.). Beacon system 16 may be designed to transmit a signal 17 to a remote device 18 when cap 14 is removed from bottle 12, which may be considered an indication the patient has taken a dose of the medication.

While shown in FIG. 1 as a medication bottle 12, other medication containers can be employed, including for example, droppers (e.g., eye), tubes, medication packets, ammo-packs, and other suitable medication containers. As shown in FIG. 1, beacon system 16 may be associated with cap 14. For example, beacon system 16 may be housed within or attached to cap 14. In some embodiments, beacon system 16 may be molded into the material (e.g., plastic) of cap 14. In other embodiments, beacon system 16 be attachable (e.g., fixedly or releasably) to cap 14. In other embodiments, beacon system 16 may be associated with bottle 12 and/or cap 14. In some embodiments, beacon system 16 may be incorporated into bottle 12 and/or cap 14 during manufacturing of the component(s). Beacon system 16 may be designed as described herein, such that the cost is sufficiently low that it can be incorporated into bottle 12 and/or cap 14 and be disposable with bottle 12 and/or cap 14 without being cost prohibitive. In some embodiments, cap 14 housing beacon system 16 may be reused by moving cap 14 from an empty bottle 12 to a new bottle when the medication prescription is refilled.

Turning to FIG. 2A, a schematic representation of beacon system 16 according to an example embodiment of the present disclosure is shown. As shown in FIG. 2A, beacon system 16 may be located within cap 14. Beacon system 16 may include a beacon 20. In some illustrative embodiments, beacon 20 may be a BLUETOOTH, BLUETOOTH Smart, BLUETOOTH 4.0, or BLUETOOTH Low Energy (BLE) beacon. In other embodiments, beacon 20 may use other protocols, for example, beacon 20 may use passive WiFi, ZIGBEE, 6LoWPAN or Z-Wave.

In some embodiments, beacon 20 may include an internal power source, as will be described in further detail below, or in other embodiments beacon system 16 may include a separate power source (not shown) operatively connected to beacon 20. For example, the power source may be a battery, capacitor, or other power storage device.

Beacon system 16 may also include electrical contacts 24 operatively connected to beacon 20 and configured to be operatively connected to a conductive strip 26. In some embodiments, as shown in FIG. 2A, conductive strip 26 may be positioned along the rim of bottle 12. Conductive strip 26 may extend part way or all the way around the rim of bottle 12. In some embodiments, the rim or all of bottle 12 may be formed using a conductive plastic or polymer (e.g., carbon filled thermoplastic elastomer), thus enabling the conductive strip 26 to be incorporated into bottle 12 as part of the initial manufacturing (e.g., injection molding) of bottle 12.

Beacon system 16 may be designed such that when cap 14 is screwed onto bottle 12, as shown illustrated in FIG. 2A, electrical contacts 24 contact conductive strip 26. And when conductive strip 26 is contacting electrical contacts 24, a closed circuit that "shorts" the electrical contacts 24 may be formed. For example, electrical contacts 24 may be connected to an input (e.g., a reset input) of beacon 20 and ground or other connection. Therefore, when cap 14 is installed on bottle 12, conductive strip 26 can short electrical contacts 24 such that beacon 20 is held in reset. When in reset, beacon 20 may remain in low-power standby mode, but when cap 14 is removed and conductive strip 26 interrupts the "short" circuit the reset can be disengaged. With the reset is disengaged, beacon 20 can wake up and begin transmitting signal 17, as will be described in detail further herein. Thus, when cap 14 is removed from bottle 12, the short circuit is broken, which is detected by beacon 20, causing beacon 20 to transmit signal 17 indicating that bottle 12 has been opened.

Figure 2B:
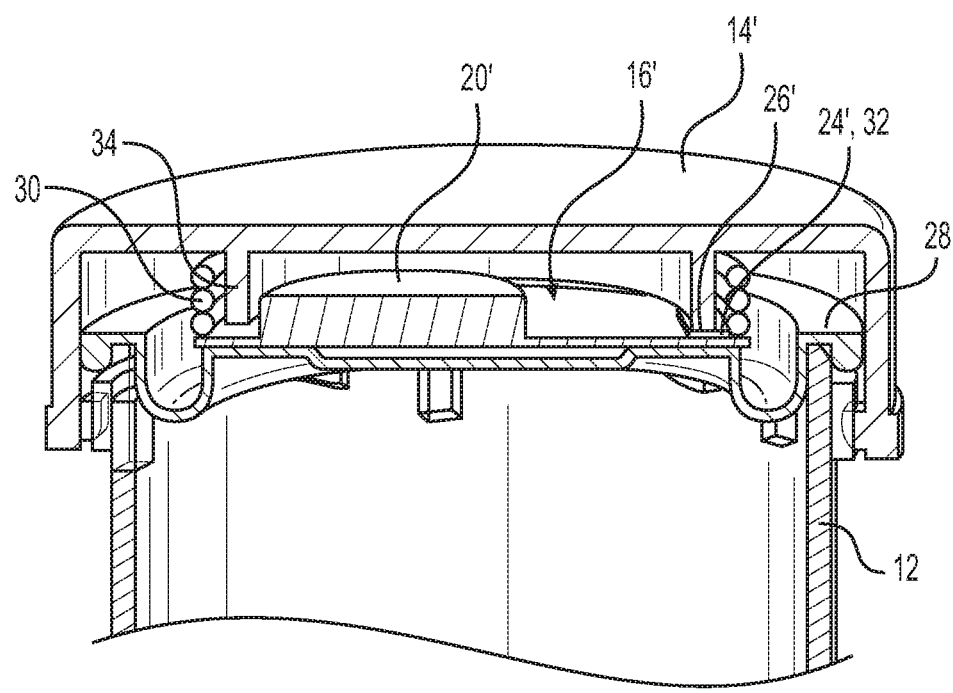
FIG. 2B is a cross-sectional perspective view of another beacon system, according to an exemplary embodiment.

Other cap designs are also contemplated. For example, FIG. 2B shows a cross-sectional perspective view of another embodiment of a cap 14' installed on bottle 12 that may be designed to detect the removal of cap 14' from bottle 12. Cap 14' may include a liner 28 that may be contained within cap 14' and designed to span the opening of bottle 12 and cover the rim of bottle 12 when cap 14' is secured to the top, as shown in FIG. 2B. Liner 28 may be designed to slide up or down within cap 14' when cap 14' is secured to or removed from bottle 12. For example, when cap 14' is removed from bottle 14, liner 28 may slide down to the bottom of cap 14' where an outer ring of liner 28 may rest on a ledge, tabs, clips, or other feature that may extend in from an outer wall of cap 14'. In some embodiments, liner 28 may be designed to slide down to the bottom of cap 14' as a result of gravity. In some other embodiments, cap 14' may include a spring 30 that forces liner 28 to slide down cap 14' when cap 14' is removed from bottle 12. When cap 14' is screwed on to bottle 14, the rim of bottle 14 will apply a force on liner 28 causing it to slide up into cap 14'. For embodiments with spring 30, the force created by screwing cap 14' on to bottle 12 may be sufficient to overcome the force applied by spring 30.

Cap 14' may also include a beacon system 16' similar to beacon system 16, which may be, for example, a print circuit board that may include a beacon 20' and electrical contacts 24' or a micro switch 32. Beacon system 16' may be secured to the upper surface of liner 28 and thus slide up and down with liner 28. As shown in FIG. 2B, cap 14' may have an inner ring 34, which is designed to contact micro switch 32 when cap 14' is secured. Contact between micro switch 32 and inner ring 34 may be designed to complete the "short" circuit resetting beacon 20' and stopping beacon 20' from transmitting signal 17. When contact between micro switch 32 and inner ring 34 is cut off, the short circuit may be broken, which is detected by beacon 20', causing beacon 20' to transmit the signal that bottle 12 has been opened.

In some embodiments, a conductive foam may be used as micro switch 32. For example, in some embodiments, the conductive foam may be conductive electrostatic discharge (ESD) foam. In some embodiments, the conductive foam may be formed of a polymer (e.g., polyurethane, polyethylene, or the like). The conductive foam may be positioned such that when cap 14' is installed on bottle 12, the conductive foam is compressed (e.g., between beacon system 16' and cap 14'), and when in the compressed state the conductive foam has a resistance sufficiently low to complete the closed circuit that "shorts" the electrical contacts 24' that may be in contact with the conductive foam. When cap 14' is removed from bottle 12, the conductive foam may return to an uncompressed state and when in the uncompressed state the conductive foam may have a resistance sufficiently high to interrupt the "short" circuit between the electrical contacts 24'.

The resistance of the conductive foam in the compressed state and the uncompressed state can be selected based on the circuit design of beacon system 16'. The resistance of the conductive foam in the compressed state can be, for example, less than about 500 kOhm, 400 kOhm, 300 kOhm, 200 kOhm, 100 kOhm, or less. The resistance of the conductive foam in the uncompressed state can be, for example, greater than about 1 MOhm, 2 MOhm, 5 MOhm, 10 MOhm, or more. In some embodiments, beacon system 16' may include an on-chip resistor having a resistance of about 1 MOhm and the resistance difference between the compressed and uncompressed state of the conductive foam may be about 10× difference from the on-board resistance of the on-board resistor. For example, the resistance of the conductive foam in the compressed state may be about 100 kOhm or less while the resistance of the conductive foam in the uncompressed state may be about 10 MOhm or more. In this example, the difference in the resistance of the conductive foam between the compressed and uncompressed state may be about 100×. It is contemplated that in other embodiments the difference in the resistance of the conductive foam in the compressed and uncompressed states may be greater than our less than about 100×, for example, about 125×, about 150×, about 175×, about 200×, about 75×, about 50×, about 25×, about 10×, about 5×, or about 2×.

The positioning of the conductive foam may vary depending on the construction of bottle 12, cap 14', beacon system 16', and/or liner 28'. In some embodiments, the conductive foam may be secured to beacon system 16', for example, across electrical contacts 24' so when cap 14' is removed it returns to its uncompressed state. In other embodiments, the conductive foam may be secured to cap 14' (e.g., inner ring 34) and aligned with electrical contacts 24' so that when cap 14' is removed the conductive foam returns to its uncompressed state and depending on the thickness of the conductive foam it may completely separate from beacon system 16' and electrical contacts 24'. The thickness of the conductive foam can vary, for example, between about 0.5 mm to about 3 mm, about 0.5 mm to about 2.5 mm, about 0.5 mm to about 2.0 mm, about 0.5 mm to about 1.5 mm, about 0.5 mm to about 1 mm, about 1.0 mm to about 3 mm, about 1.5 mm to about 3 mm, about 2.0 mm to about 3 mm, about 2.5 mm to about 3 mm, about 1 mm to about 2.5 mm, about 1.5 mm to about 2.0 mm.

In some embodiments, a coversheet (not shown) may be positioned between the beacon system 16' and cap 14' may cover at least a portion of beacon system 16' and micro switch 32 (e.g., the conductive foam). The coversheet may protect inner ring 34 of cap 14' as well as the beacon system 16' from being damaged. The coversheet may also provide a wider contact surface for initiating the compression of the conductive foam in the event the conductive foam is not precisely aligned, for example, with inner ring 34 of cap 14'. In some embodiments, the conductive foam may be secured to the coversheet.

In some embodiments, instead of a micro switch 32, electrical contacts 24' and a conductive strip 26' may be used to complete and cutoff the short circuit as described herein with regard to electrical contacts 24 and conductive strip 26. Electrical contacts 24' may be positioned on a surface of beacon system 16 (e.g., of the print circuit board) while conductive strip 26' may be positioned on inner ring 34 or vice versa.

Cap 14' and liner 28 may be made of the same material or different materials. For example, in some embodiments, cap 14' may be made of a higher density more rigid material (e.g., high-density polyethylene) while liner 28 is made of a lower density more flexible material (e.g., low-density polyethylene). The flexibility of liner 28 may enable it to act as a liner and a seal when cap 14' is installed on bottle 12, thereby reducing or preventing contaminants or moisture from entering bottle 12. For example, inner ring 34 and the rim of bottle 12 may act on liner 28 when cap 14' is installed, as shown in FIG. 2B, to deflect liner 28 creating a spring like force within liner 28 that cause a seal to form between liner 28 and the rim of bottle 12.

For the purposes of this disclosure, all previous and subsequent description in reference to cap 14, beacon system 16, beacon 20, electrical contacts 24, and conductive strip 26 are all equally applicable to cap 14', beacon system 16', beacon 20', electrical contacts 24', and conductive strip 26', and vice versa, besides where a distinction is noted.

It is contemplated that other techniques or mechanisms may be used to detect the removal of cap 14 from bottle 12. For example, some embodiments may utilize a pressure sensor positioned between cap 14 and bottle 12 and when the pressure changes (e.g., when cap 14 is removed), the pressure sensor may interrupt the "short" circuit causing beacon 20 to transmit the signal that bottle 12 has been opened.

In some embodiments, the removal of cap 14 from bottle 12 may trigger a change in signal 17 transmitted from beacon 20 rather than simply initiating the transmitting of signal 17 from beacon 20. For example, in some embodiments, beacon system 16 may be designed to transmit one identifiable signal while cap 14 is installed on bottle 12 and then change to or begin transmitting a second identifiable signal once cap 14 is removed from bottle 12. The transmission of the second identifiable signal may be recognized as an indication the patient has taken a dose of the medication.

These one or more signals may be received by a remote device 18 (e.g., a smart phone) or other associated device, which can use the event (i.e., receiving of the sign or a change of the signal) as evidence that the patient has taken the medication. Beacon 20 may be a low-energy radio transponder.

Figure 2C:
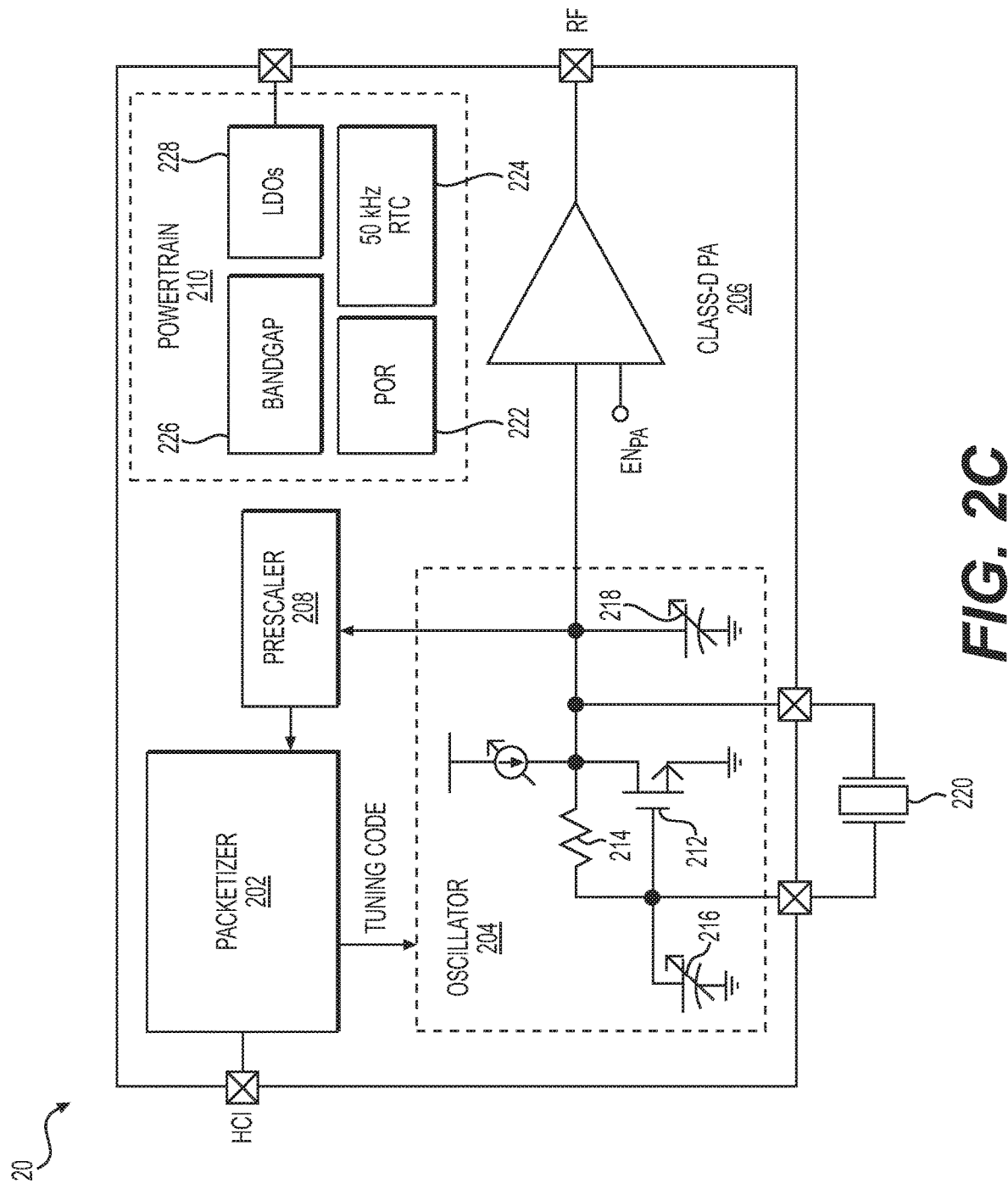
FIG. 2C is a schematic diagram of a beacon, in accordance with an example embodiment.

Now the operation of an exemplary embodiment of beacon 20 will be described with reference to FIG. 2C. As illustrated in FIG. 2C, beacon 20 may include a packetizer 202 (e.g., a BLE packetizer), an oscillator 204, a powertrain 210, and an amplifier 206. These components, as described herein, may be used to transmit signal 17 as shown in FIG. 1 from beacon system 16. In some embodiments, beacon 20 may be enabled to receive a signal from another device (e.g., remote device 18). In other embodiments, beacon 20 may be configured to operate as solely a transmitter. For example, beacon 20 may transmit a signal that may be received by remote device 18, without pairing with remote device 18.

Embodiments of beacon 20 with only transmitting capability may have decreased power consumption due to the elimination of the receiving hardware. In addition, eliminating the receiving hardware may also decrease the manufacturing cost of beacon 20. Furthermore, the size of beacon 20 may also be decreased due to the elimination of the receiving hardware.

Returning to FIG. 2C, packetizer 202 may receive a signal via host controller interface (HCI). In some embodiments, packetizer 202 may interface with a processor (not shown) of beacon system 16 or may interface with electrical contacts 24. In some embodiments, the signal that packetizer 202 receives may include data, which may be included in the signal transmitted by beacon 20. For example, in some embodiments where packetizer 202 interfaces with a process, the signal received from the processor may include parameters such as encryption parameters, modulation parameters, a mode of operation of beacon 20, packet type, etc. Additional parameters may be used to configure beacon 20 to generate a specific signal, which may be transmitted by beacon 20.

In some embodiments, the signal received via HCI may be indicative of a mode of operation of beacon 20. For some embodiments, the mode of operation may depend on the functionality of beacon 20. In some embodiments, the functionality of beacon 20 may be predetermined, for example, beacon 20 may be used in a specific application.

In some embodiments, the modes of operation of beacon 20 may include an advertising mode in which an advertising protocol (e.g., BLE) is used to periodically transmit data packets referred to as advertising packets (also referred to herein as "advertisement packets"). The advertising packets may carry data indicative of beacon 20 (e.g., a unique identification number (UID)).

In some embodiments, the mode of operation of beacon 20 may affect its power consumption. For example, beacon 20 may decrease power consumption by using advertising protocols. Advertising protocols may enable beacon 20 to operate with low power consumption by periodically broadcasting signal 17 during certain time intervals. For example, in some embodiments, beacon 20 may only advertise when cap 14 is removed and the "short" circuit is interrupted. During time intervals where beacon 20 is not broadcasting a signal, beacon 20 may be idle or turn-off in a standby mode (e.g., hibernate). By turning on only when transmitting a signal in active transmit mode, beacon 20 may decrease its power consumption, which may be advantageous for devices with a finite power source. As such, advertising protocols enable beacon 20 to advertise data to one or more remote devices 18 while maintaining low power consumption for beacon 20.

BLE protocols may include different types of advertising packets. The advertising packet type may specify, for example, a configuration of beacon 20. For example, the advertising packet type may specify whether beacon 20 is connectable and/or scannable. A connectable beacon 20 may pair with another device (e.g., BLUETOOTH device), and a scannable beacon 20 may broadcast and advertising packet in response to receiving a scan request from another device. (e.g., BLUETOOTH device). Furthermore, an advertising packet may be a directed packet. For example, a directed packet may include the beacon 20 address and remote device's 18 address, whereas an undirected packet may not be directed toward a particular remote device 18 (i.e., receiver).

The configuration of beacon 20, which may be specified by the advertising packet type, may also affect the power consumption of beacon 20. For example, beacon 20 in a connectable and scannable configuration may use more power than a beacon 20 in a non-connectable and non-scannable configuration. This is because beacon 20 in a connectable and scannable configuration has a longer active transmit time than beacon 20 operating in the non-connectable and non-scannable configuration.

As explained above, in some embodiments, beacon 20 may operate only as a transmitter and therefore may not be able to operate in a connectable configuration. Furthermore, in some embodiment, the transmitter may not be able to receive scan requests from other devices. Thus, in some embodiments, beacon 20 may be operating in a non-connectable and non-scannable configuration in order to decrease power consumption.

There are additional advantages besides lower power consumption that may be achieve by beacon 20 using BLE advertising protocols. For example, remote device 18 may discover BLUETOOTH device located near remote device 18 faster (and consuming less energy) using advertising protocols than by using other protocols. Advertising protocols may use three fixed channels of a wireless spectrum, e.g., the 2.4 GHz wireless spectrum. Thus, by not scanning the full wireless spectrum, remote device 18 may detect other BLUETOOTH device over the three fixed channels, enabling for the receiving and sending of BLE advertisement packets faster than the other protocols.

Returning now to FIG. 2C, packetizer 202 may use the data included in the signal received via HCI to generate a data signal, which may include one or more data packets. Packetizer 202 may receive instructions to generate a data signal including one or more data packets according to an advertising protocol. In some embodiments, the instructions may detail the type of advertising event to broadcast. For example as explained above, the type of advertising event may determine whether the device is connectable and/or scannable, and/or whether the packet is directed. In an example, packetizer 202 may receive data indicative of instructions to generate a data signal that includes a non-connectable, non-scannable, and undirected advertising event.

Oscillator 204 may generate an RF carrier signal that may carry the data signal generated by packetizer 202. The RF signal carrying the data may then be broadcasted by beacon 20. As illustrated in FIG. 2C, oscillator 204 may be a free-running oscillator, which may be used to directly generate an RF carrier signal. Thus, a free-running oscillator is an alternative to using a frequency synthesizer (i.e., Phase Locked Loop (PLL) synthesizer) to generate an RF carrier signal. Typically, a frequency synthesizer, which also includes a frequency reference circuit, may dissipate a significant portion of a transmitter's power. Accordingly, using a free-running oscillator may result in considerable power savings, which may be advantageous in achieve low power consumption operation for beacon 20.

Both the turn-on time for the frequency synthesizer to lock to its frequency reference and the turn-on time of its frequency reference circuit may be significant compared to the packet duration. Therefore, the turn-on time (i.e., time to go from sleep mode to active transmit mode) for a transmitter using a frequency synthesizer may be greater than a transmitter using a free-running oscillator. A longer turn-on time may result in greater power dissipation. Accordingly, using the free-running oscillator, which may have a reduced turn-on time compared to a frequency synthesizer, may result in further power savings.

The free-running oscillator may directly generate the RF carrier signal, which may have a frequency within a wireless spectrum, e.g., the 2.4 GHz wireless spectrum. For example, the free-running oscillator may directly generate a RF carrier signal that has a frequency of one of the three channels in the 2.48 GHz band that are allocated to BLE advertising protocols according to BLUETOOTH specifications. The three channels are specified as 1 MHz wide channels with frequencies of 2.402 GHz, 2.480 GHz, and 2.426 GHz.

Note that the example oscillator provided in FIG. 2C and the accompanying description herein is for illustrative purposes only and should not be considered limiting. For instance, beacon 20 may include more than one free-running oscillator. In some embodiments, beacon 20 may include three free-running oscillators, each of which may be used to generate a carrier signal at a frequency of the three BLE channels. In such examples, beacon 20 may utilize methods such as multichannel transmission and frequency hopping.

In some embodiment, free-running oscillator 204 may be a Pierce oscillator, which is illustrated in FIG. 2C. The Pierce oscillator 204 may include a transistor 212, a biasing resistor 214, capacitors 216 and 218, and a resonator 220. Resonator 220, which may extend out from beacon 20, may be used as a filter to filter the oscillation frequency. Further, the total capacitance of the two capacitors 216 and 218, as seen by the resonator, may be referred to as the "load" capacitance." The load capacitance may affect how far the oscillator loop is resonating, relative to the desired resonant frequency. Accordingly, selectively choosing the resonator, which may have a specific load capacitance requirement, may determine the oscillation frequency.

In some embodiments, the resonator 220 may be a thin-film bulk acoustic resonator (FBAR). An FBAR resonator 220 may include a piezoelectric thin film between two metal layers. FBAR are high-Q resonators that may have a stable and a low phase-noise center frequency, which may be the oscillation frequency. In some embodiments, FBAR resonators may have a Q of several hundred. In other embodiments, FBAR resonators may have an (unloaded) Q of over one thousand. Further, temperature compensation may be used to maintain the center frequency of FBAR resonator 220 at the frequency of the wireless channel.

The example resonator 220 shown in FIG. 2C and the accompanying description herein is for illustrative purposes only and should not be considered limiting. Any suitable resonator may be used. For example, the resonator may be any high frequency resonator, which may provide an oscillation frequency with stability and an accuracy that may meet BLUETOOTH standards. In other examples, the resonator may be a crystal resonator. For one example, the resonator may be a quartz resonator.

As noted above, the RF carrier signal generated by oscillator 204 may be used to carry the data signal generated by packetizer 202. More specifically, the data signal generated by packetizer 202 may act as a tuning code, which may have a specific symbol rate. Further, the tuning code may be used to directly modulate the RF carrier signal. Accordingly, the modulated RF carrier signal may carry the data signal generated by packetizer 202. Within examples, the tuning code may modulate the RF carrier signal according to at least BLE's protocols.

For instance, BLE protocols specify using Gaussian Frequency Shift Keying (GFSK) as the modulation scheme to modulate the RF carrier signal. Accordingly, the tuning code may be used to modulate the RF carrier signal to two different frequencies of the same advertising channel according to GFSK. Additionally and/or alternatively, the tuning code may be used to modulate the RF carrier signal to two different frequencies of the same advertising channel according to Binary Frequency Shift Keying (BFSK). Oscillator 204 may include a bank of switched capacitors, represented by variable capacitors 216 and 218 in FIG. 2C, which may be used to adjust the load capacitance of Pierce oscillator 204. As explained above, adjusting the load capacitance of Pierce oscillator 204 may adjust the oscillation frequency. The digital data signal, indicative of digital "0" and "1", may be used to modify the load capacitance of Pierce oscillator 204, such that oscillator 204 may generate a modulated signal of two frequencies, one of which corresponds to digital "0" and the other to digital "1."

The modulated RF signal, carrying the data signal, may be transmitted to a class-D power amplifier 206, as illustrated in FIG. 2C. In some embodiments, at least a portion of the modulated signal may be transmitted to a prescaler 208. Prescaler 208 may scale the signal and provide the scaled signal to packetizer 202, where it may be used as a clock source. For example, prescaler 208 may scale down the 2.48 GHz signal to a 1 Mhz or 8 Mhz signal. By using a portion of the carrier signal as a clock source for packetizer 202, there may be no need for a separate timing source for packetizer 202, thereby further decreasing power consumption.

As illustrated in FIG. 2C, the modulated RF carrier signal may be amplified using class-D power amplifier 206. The amplified signal may then be transmitted to the radio (represented as "RF" in FIG. 2C) where it may be broadcast over the air as signal 17. As explained above, in some embodiments, beacon 20 may be operating in advertising mode, which involves beacon 20 periodically transmitting advertising packets. Accordingly, the broadcasted RF signal may include advertisement packets, which may be received by one or more remote devices 18.

Beacon 20 may be powered by powertrain 210. Powertrain 210 may include a low dropout regulator (LDO) 228, a power on reset (PoR) 222, a bandgap voltage reference (Bandgap) 226, and a real time clock (RTC) 224. Note that the RTC 224 may have a low frequency and may operate without a crystal reference, as packetizer 202 may use a signal from oscillator 204 as described above.

Beacon 20, as described herein, may transmit a signal to one or more remote devices 18 by carrying out one or more steps or functions, as described below. First, beacon 20 may generate, based on data, a data signal comprising one or more data packets. In some embodiments, the data may include information such as encryption parameters, modulation parameters, mode of operation of the device, packet type etc. In some embodiments, the data packet may be a non-connectable, non-scannable advertising packet. For the next step, beacon 20 may generate an RF signal using an oscillator circuit. Next, beacon 20 may directly modulate the RF signal, based on the data signal, to generate a modulated RF signal. As noted above, the modulated RF signal may conform to BLE protocols. Further, the RF signal may be directly modulated by using the data signal to adjust the load capacitance of oscillator 204 using the bank of switched capacitors. For the next step, beacon 20 may amplify the modulated RF signal. Next, beacon 20 may broadcast the amplified RF signal (i.e., signal 17) on the wireless channel. As described here, the wireless channel may be a channel in the 2.4 GHz spectrum.

As discussed herein, beacon 20 can be configured to turn on and transmit signal 17 when cap 14 is removed. In some embodiments, beacon 20 may transmit signal 17 for the duration cap 14 is while in other embodiments beacon 20 may transmit signal 17 for a fixed duration once cap 14 is removed.

As described herein, in some embodiments, remote device 18 can be detected by beacon 20 when it comes in range and opens communication. Various protocols may be used for this, including for example, proximity beacon application program interface (API) and Eddystone protocol available from Google. As will be appreciated from this disclosure, other communication protocols may be utilized.

In some embodiments, beacon 20 can broadcast encrypted data. For example, system 10 can include an encryption key, such as a QR or bar code on bottle 12 or cap 14. Remote device 18, or other device, can be used to scan the code (e.g., using an on-board camera), input the code, or otherwise receive the encryption key, and use the key to receive encrypted data from beacon 20. In this way, only authorized devices may receive and decrypt data from signal 17, which can increase security, for example when undirected transmissions are used.

In some embodiments, beacon 20 may broadcast signal 17 not just when cap 14 is removed from bottle 12, but instead beacon 20 may broadcast signal 17 (i.e., send data) that may be received by remote device 18 when idle. For example, beacon 20 may broadcast an idle status signal that may be terminated when beacon 20 begins broadcasting the signal indicating cap 14 is removed.

Remote device 18 may be a smart phone, a smart watch, or other programmable user interface device with a mobile operating system. The smartphone or device may include a controller. The controller may include one or more hardware processors, such as one or more central processing units (CPUs). The processor(s) may execute a set of instructions to perform operations. The set of instructions may be programmed and stored in one or more memory devices. Examples of memory devices include non-volatile memory (e.g., a flash memory), volatile memory (e.g., a random access memory (RAM)), and other memory components. In some embodiments, the controller may be configured run programmed instructions or software to execute operations, as described herein. The controller may also include one or more interfaces to communicate with beacons of packets or packet bundles.

Remote device 18 may run or execute a programmable application ("the app") designed to interface with beacon system 16. The app may be downloadable to remote device 18 via the internet or an app store, for example, the PLAY STORE operated by Google.

The app may be programmed with a wide range of functionality. For example, the app may be programmed to receive medication prescription information. The medication prescription information may include, for example, the patient's name, patient identifier (e.g., a date of birth), the type of medication, the strength or the dose of medication (e.g., 100 mg, 200 mg, one pill, two pill, etc.), the frequency of dose (e.g., daily, twice daily, as needed, etc.), the duration of the prescription (e.g., three days, four days, five days, six days, 1 week, 2 weeks, indefinitely, etc.), the number of doses, the number of refills prescribed, the route by which it is to be delivered (e.g., orally), the time of day doses are to be taken, or other relevant information (e.g., take with food, take with water, etc.). The app may receive the medication prescription information in a variety of ways. For example, the medication prescription information may be transmitted to the app when the prescription is picked up at the pharmacy or downloaded (e.g., via an internet based patient login). Alternatively, the medication prescription information could be contained on the label (e.g., written out, as a bar code, or a QR label) and may be scanned by remote device 18 (e.g., using an on-board camera) and loaded into the application. The medication prescription information could also be input manually by a patient, a caregiver, or other individual by typing it in or speaking into remote device 18.

In some embodiments, remote device 18 may upload and/or cross-check some or all of the medication prescription information to patient's medical record by accessing, for example, the cloud where the patient's medical records may be stored. This can enable a patient's medical records to be updated real time with all of their medication prescriptions.

The app may be programmed to detect each time a signal from beacon 20 is transmitted, which is representative that the medication is being taken, and log the time and date at which the medication is taken. If the patient is taking multiple medications the app may be programmed to differentiate the signal from each beacon 20 and log the time and date corresponding to the correct medication. For some embodiments, the app may be programmed to display a prompt asking the patient to confirm they took the medication.

For some embodiments, the app may be programmed to remind the patient to take a medication. For example, if the app has not detect a signal indicating cap 14 has been removed within a prescribed window in which the patient was supposed to take the medication, then the app can prompt the user to take the medication.

The app may be programmed to prompt the user in a variety of ways. For example, remote device 18 may display a message on the screen, ring, vibrate, or flash light (e.g., flash screen or flash on-board camera flash). The app may be programmed to escalate the intrusiveness of the prompt based on various factors (e.g., the urgency or importance of the medication or the length of time that has passed since an initial prompt was issued. The app may be programmed to enable the patient to override a prompt. For example, if the patient took the medication, but remote device 18 missed the signal transmission from beacon 20 because it was out of range, for example, the patient may input that they took the medication.

In some embodiments, the app may be programmed to send a prompt reminding the patient in advance of when they should be taking a medication. This may be advantageous if a medication requires that the user eat before or take with a drink so the reminder can enable the patient to plan accordingly.

In some embodiments, the app may be programmed to send a prompt to the patient if the app detects that the patient may be taking the wrong medication. For example, if the patient is on two or more medications and at the time the patient is scheduled to a take a first medication the patient opens the bottle for a second medication, the app may prompt the patient to the error.

In some embodiments, the app may be programmed to prompt the patient with instructions corresponding to taking of the medication. The corresponding instructions may include, for example, take with food, take with water, take with a certain quantity of water, do not drink alcohol while taking, do not drive after taking, etc.

For some embodiments, the app may be programmed to prompt the patient if the patient is taking the medication outside a prescribed window. For some embodiments, where the patient's prescription "is as needed," the app may be programmed to prompt the patient to input the dose amount of the medication taken each time bottle 12 is opened so the doses can be logged. For some embodiments, the app may keep track of the number of doses left in bottle 12 and may prompt the patient to request a refill prior to being empty or in some embodiments the app may generate and send a refill request directly to a caregiver and/or a pharmacy.

For some embodiments, the app may be programmed to ask the patient questions associated with the medication prescription. For example, the app may ask the user to confirm they will not be drinking alcohol if the medication cannot be taken while drinking or the app may ask the user to confirm they will not be operating a vehicle if the medication cannot be taken if a patient will be operating a vehicle. For some embodiments, the app may ask the patient whether the patient is experiencing any side effects that may be associated with the medication. Whether the patient is experiencing side effects may then be transmitted to a caregiver (e.g., doctor, psychiatrist, nurse practitioner, etc.), which may use this information to evaluate and/or modify the prescription as needed.

For some embodiments, the app may be programmed to prompt the patient if the app determines that the patient is leaving home without their medication. For example, the app may be programmed to recognize the patient's home or other known wifi, GPS location, or vehicle BLUETOOTH connection and if the app determines the patient is moving (e.g., based on loss or change of wifi signal, change in GPS location, or detection of vehicle Bluetooth connection) and the app is not receiving a signal (e.g., a status signal from beacon 20) the app may prompt the user that their medication is not with them. The app may be programmed only to prompt the user if the patient is going to need to take the medication in the near future (e.g., the next two hours, next four hours, next six hours, or next eight hours).

The functionality of the app may be configurable by the patient. In other words, the patient may select what prompts they want to receive and what prompts they do not. For some embodiments, some prompts may be compulsory while other prompts may be selectable. For some embodiments a caregiver may select what prompts are active and not active.

Although system 10 is described primarily in reference to prescription medications, system 10 may also be used in conjunction with non-prescription medications, vitamins, supplements, etc. And, although system 10 is described primarily in reference to a pill or capsule bottle, system 10 may be incorporated into other medication containers, bottles, or dispensers. For example, system 10 may be used with eye drop bottles, ointment tubes, or other medication containers.

Figure 3:
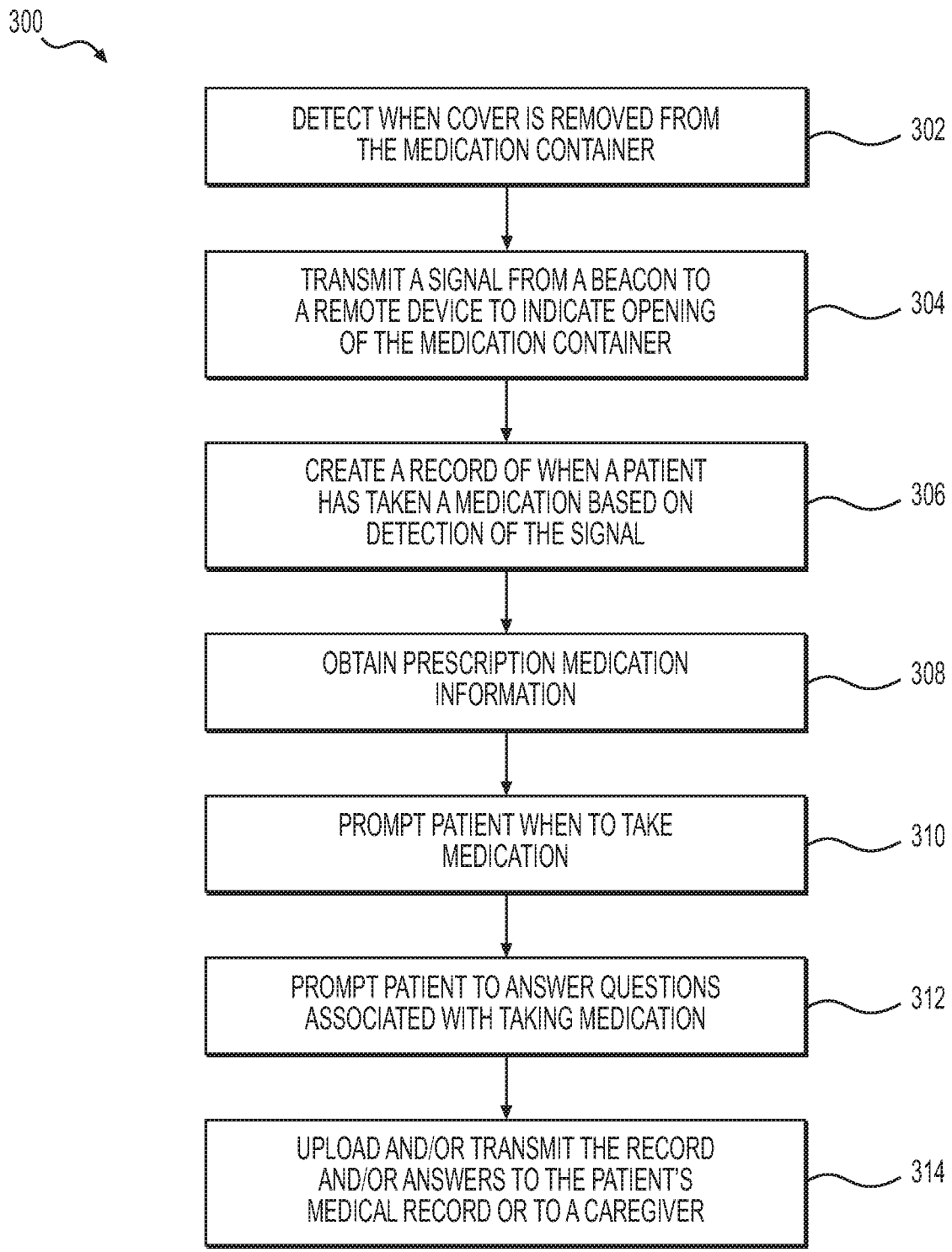
FIG. 3 is a flow chart illustrating a method for monitoring medication adherence and compliance, according to an exemplary embodiment

FIG. 3 shows an illustrative process 300 for monitoring medication adherence and compliance, consistent with embodiments of the present disclosure. Process 300 may be implemented using any of the exemplary embodiments of system 10 described herein, including those illustrated and described with reference to FIGS. 1 and 2A, 2B, and 2C.

At step 302, the system can detect when the cover or cap is removed from the medication container. For example, as discussed above, the removal of the cap may open a closed circuit thus resetting the beacon. At step 304, the beacon can transmit based on the detection, a signal from the beacon to a remote device, which indicates the opening of the medication bottle. Optionally at step 306, an application running on the remote device may recognize the signal as an indication that a patient has taken a medication from the bottle and create a record of when the patient takes the medication based on detection of the signal. Optionally at step 308, the remote device may obtain prescription medication information by scanning a label of the medication, inputting by the user, or transmitting by the pharmacy, as described herein. Optionally at step 310, the remote device may prompt the patient when to take the medication. For example, the remote device may prompt the patient with a reminder to take the medication in advance or may prompt the patient to take the medication if the patient has not taken the medication during a prescribed window. Optionally at step 312, the remote device may prompt the patient to answer questions associated with taking the medication, as described herein. Optionally at step 314, the remote device may upload or transmit the record and/or the patient's answers to the patient's medical record or to a caregiver. Process 300 as described herein may optionally include numerous other steps utilizing the above described functionality of system 10 and the application interfacing with beacon system 16. Process 300 may vary based on the functionality selected by the patient and/or the caregiver.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

Computer programs, program modules, and code based on the written description of this specification, such as those used by the remote device, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

That which is claimed is:

1. A method comprising:
   obtaining, by a computing device, prescription information associated with one or more medications for an individual;
   receiving, by the computing device using a wireless receiver, a signal from a medication container indicating an opening of the medication container, the medication container associated with the individual;
   in response to receiving the signal indicating the opening of the medication container:
      determining, by the computing device, an identity of the medication container based on the signal;
      determining, by the computing device, a medicine type based on the identity of the medication container;
      determining, by the computing device, first prescription information of the prescription information, the first prescription information associated with the medicine type and based at least in part on the prescription information associated with the individual; and
      outputting, by the computing device, a notification based on the determined first prescription information associated with the medicine type.

2. The method of claim 1, further comprising:
   determining, by the computing device, the medicine type is a wrong medicine type based on the identity of the medication container and the prescription information; and
   wherein the notification comprises a notification indicating the medicine type is the wrong medicine type.

3. The method of claim 1, further comprising:
   determining one or more medication instructions corresponding to the medicine type based on the prescription information; and
   wherein the notification comprises one or more of the one or more medication instructions.

4. The method of claim 3, wherein the one or more medication instructions comprises one or more of (i) medication instructions to take the medicine type with food or water, (ii) medication instructions to not drink alcohol while taking the medicine type, or (iii) medication instructions to not drive or operate heavy machinery after taking the medicine type.

5. The method of claim 4, further comprising outputting a request for confirmation that the individual is complying with the one or more medication instructions.

6. The method of claim 1, further comprising:
   requesting, by the computing device from the individual, information about side effects experienced by the individual; and
   transmitting the information about the side effects to a remote computing device.

7. The method of claim 1, further comprising obtaining, by the computing device, updated prescription information for the individual based on the medicine type.

8. The method of claim 1, further comprising:
   requesting, by the computing device from the individual, information about a dose size taken of the medicine type; and
   storing the dose size.

9. The method of claim 8, further comprising:
   determining a number of doses remaining in the medication container; and
   transmitting a request for a prescription refill to a remote computing device based on the number of doses remaining in the medication container.

10. The method of claim 1, wherein the computing device is remote from the medication container.

11. A device comprising:
    a wireless receiver;
    a non-transitory computer-readable medium; and
    a processor communicatively coupled to the wireless receiver and the non-transitory computer-readable medium, the processor configured to execute processor-executable instructions stored in the non-transitory computer-readable medium to:
    obtain prescription information associated with one or more medications for an individual;
    receive, using the wireless receiver, a signal from a medication container indicating an opening of the medication container, the medication container associated with the individual;
    in response to receipt of the signal indicating the opening of the medication container:
       determine an identity of the medication container based on the signal;
       determine a medicine type based on the identity of the medication container;
       determine first prescription information of the prescription information, the first prescription information associated with the medicine type and based at least in part on the prescription information associated with the individual; and
       output a notification based on the determined first prescription information associated with the medicine type.

12. The device of claim 11, wherein the processor is further configured to execute processor-executable instructions stored in the non-transitory computer-readable medium to:
    determine the medicine type is a wrong medicine type based on the identity of the medication container and the prescription information; and
    wherein the notification comprises a notification indicating the medicine type is the wrong medicine type.

13. The device of claim 11, wherein the processor is further configured to execute processor-executable instructions stored in the non-transitory computer-readable medium to:
    determine one or more medication instructions corresponding to the medicine type based on the prescription information; and
    wherein the notification comprises one or more of the one or more medication instructions.

14. The device of claim 13, wherein the one or more medication instructions comprises one or more of (i) medication instructions to take the medicine type with food or water, (ii) medication instructions to not drink alcohol while taking the medicine type, or (iii) medication instructions to not drive or operate heavy machinery after taking the medicine type.

15. The device of claim 14, wherein the processor is further configured to execute processor-executable instructions stored in the non-transitory computer-readable medium to output a request for confirmation that the individual is complying with the one or more instructions.

16. The device of claim 11, wherein the processor is further configured to execute processor-executable instructions stored in the non-transitory computer-readable medium to:
   request, from the individual, information about side effects experienced by the individual; and
   transmit the information about the side effects to a remote computing device.

17. The device of claim 11, wherein the processor is further configured to execute processor-executable instructions stored in the non-transitory computer-readable medium to obtain updated prescription information for the individual based on the medicine type.

18. The device of claim 11, wherein the processor is further configured to execute processor-executable instructions stored in the non-transitory computer-readable medium to:
   request, from the individual, information about a dose size taken of the medicine type; and
   storing the dose size.

19. The device of claim 18, wherein the processor is further configured to execute processor-executable instructions stored in the non-transitory computer-readable medium to:
   determine a number of doses remaining in the medication container; and
   transmit a request for a prescription refill to a remote computing device based on the number of doses remaining in the medication container.

20. A non-transitory computer-readable medium comprising processor-executable instructions to cause a processor to:
   obtain prescription information associated with one or more medications for an individual;
   receive, using a wireless receiver, a signal from a medication container indicating an opening of the medication container, the medication container associated with the individual;
   in response to receipt of the signal indicating the opening of the medication container:
      determine an identity of the medication container based on the signal;
      determine a medicine type based on the identity of the medication container;
      determine first prescription information of the prescription information, the first prescription information associated with the medicine type and based at least in part on the prescription information associated with the individual; and
      output a notification based on the determined first prescription information associated with the medicine type.

21. The non-transitory computer-readable medium of claim 20, further comprising processor-executable instructions to cause a processor to:
   determine the medicine type is a wrong medicine type based on the identity of the medication container and the prescription information; and
   wherein the notification comprises a notification indicating the medicine type is the wrong medicine type.

22. The non-transitory computer-readable medium of claim 20, further comprising processor-executable instructions to cause a processor to:
   determine one or more medication instructions corresponding to the medicine type based on the prescription information; and
   wherein the notification comprises one or more of the one or more medication instructions.

23. The non-transitory computer-readable medium of claim 22, wherein the one or more medication instructions comprises one or more of (i) medication instructions to take the medicine type with food or water, (ii) medication instructions to not drink alcohol while taking the medicine type, or (iii) medication instructions to not drive or operate heavy machinery after taking the medicine type.

24. The non-transitory computer-readable medium of claim 23, further comprising processor-executable instructions to cause a processor to output a request for confirmation that the individual is complying with the one or more instructions.

25. The non-transitory computer-readable medium of claim 20, further comprising processor-executable instructions to cause a processor to:
   request, from the individual, information about side effects experienced by the individual; and
   transmit the information about the side effects to a remote computing device.

26. The non-transitory computer-readable medium of claim 20, further comprising processor-executable instructions to cause a processor to obtain updated prescription information for the individual based on the medicine type.

27. The non-transitory computer-readable medium of claim 20, further comprising processor-executable instructions to cause a processor to:
   request, from the individual, information about a dose size taken of the medicine type; and
   storing the dose size.

28. The non-transitory computer-readable medium of claim 27, further comprising processor-executable instructions to cause a processor to:
   determine a number of doses remaining in the medication container; and
   transmit a request for a prescription refill to a remote computing device based on the number of doses remaining in the medication container.

* * * * *